(12) United States Patent
Kucharczyk et al.

(10) Patent No.: US 12,178,684 B2
(45) Date of Patent: Dec. 31, 2024

(54) METHOD AND SYSTEM FOR THREE-DIMENSIONAL IMAGING

(71) Applicant: DENTSPLY SIRONA Inc., York, PA (US)

(72) Inventors: Ronny Kucharczyk, Worms (DE); Björn Voss, Bensheim (DE)

(73) Assignee: Dentsply Sirona Inc., York, PA (US)

( * ) Notice: Subject to any disclaimer, the term of this patent is extended or adjusted under 35 U.S.C. 154(b) by 701 days.

(21) Appl. No.: 17/427,334

(22) PCT Filed: Jan. 22, 2020

(86) PCT No.: PCT/EP2020/051456
§ 371 (c)(1),
(2) Date: Jul. 30, 2021

(87) PCT Pub. No.: WO2020/156893
PCT Pub. Date: Aug. 6, 2020

(65) Prior Publication Data
US 2022/0133445 A1 May 5, 2022

(30) Foreign Application Priority Data
Jan. 30, 2019 (EP) .................................... 19000057

(51) Int. Cl.
*G06K 9/62* (2022.01)
*A61B 5/00* (2006.01)
(Continued)

(52) U.S. Cl.
CPC ............ *A61C 9/006* (2013.01); *A61B 5/0088* (2013.01); *G06V 10/17* (2022.01); *G06V 10/757* (2022.01)

(58) Field of Classification Search
CPC .. A61C 9/00; A61C 13/08; A61B 5/00; A61B 5/107
See application file for complete search history.

(56) References Cited

U.S. PATENT DOCUMENTS

| 4,837,732 A | 6/1989 | Brandestini |
| 7,940,260 B2 | 5/2011 | Kriveshko |
(Continued)

FOREIGN PATENT DOCUMENTS

| JP | 2003532485 A | 11/2003 |
| JP | 2008504049 A | 2/2008 |
(Continued)

OTHER PUBLICATIONS

International Search Report; PCT/EP2020/051456; Mar. 30, 2020 (completed); Apr. 30, 2020 (mailed).
(Continued)

*Primary Examiner* — Howard D Brown, Jr.
(74) *Attorney, Agent, or Firm* — SCHWEGMAN LUNDBERG & WOESSNER, P.A.

(57) ABSTRACT

A method and system for dynamically providing visual feedback about a quality of data collected during intra-oral scanning Images or light patterns are projected onto an object such as teeth for 3D measurement and for relaying feedback about a quality of the 3D measurement to a user. In this way unsuccessful registrations surface areas of the teeth that have not been acquired yet may be corrected by informing the user to repeat scans at corresponding locations in the intra-oral cavity.

13 Claims, 5 Drawing Sheets

(51) Int. Cl.
*A61C 9/00* (2006.01)
*G06T 7/11* (2017.01)
*G06V 10/10* (2022.01)
*G06V 10/75* (2022.01)

(56) References Cited

U.S. PATENT DOCUMENTS

| | | |
|---|---|---|
| 9,838,670 B2 | 12/2017 | Glinec |
| 2006/0269896 A1* | 11/2006 | Liu .................. G01B 11/24 433/29 |
| 2011/0019155 A1* | 1/2011 | Daniel ................ G03B 21/26 353/28 |
| 2015/0017598 A1* | 1/2015 | Wu .................. G01B 11/2518 433/29 |
| 2016/0014396 A1* | 1/2016 | Glinec ................ H04N 23/698 433/29 |
| 2017/0224272 A1* | 8/2017 | Liu .................... A61B 5/4547 |
| 2018/0318051 A1 | 11/2018 | Lu |
| 2019/0029784 A1* | 1/2019 | Moalem ............. A61C 13/0004 |
| 2023/0355360 A1* | 11/2023 | Jensen ................ A61B 5/7455 |

FOREIGN PATENT DOCUMENTS

| | | |
|---|---|---|
| JP | 2009078133 A | 4/2009 |
| JP | 2009523547 A | 6/2009 |
| JP | 2012055695 A | 3/2012 |
| JP | 2014521163 A | 8/2014 |
| JP | 2014522249 A | 9/2014 |
| JP | 2017533000 A | 11/2017 |
| JP | 2019097851 A | 6/2019 |
| JP | 6764783 B2 | 10/2020 |
| WO | 2007084647 A2 | 7/2007 |

OTHER PUBLICATIONS

International Preliminary Report on Patentability; PCT/EP2020/051456; Mar. 30, 2020 (completed); Apr. 30, 2020 (mailed).
Written Opinion of the International Searching Authority; PCT/EP2020/051456; Mar. 30, 2020 (completed); Apr. 30, 2020 (mailed).
Japanese Office Action dated Dec. 25, 2023.
Japanese Office Action dated Jun. 4, 2024.

* cited by examiner

METHOD AND SYSTEM FOR THREE-DIMENSIONAL IMAGING

CROSS-REFERENCE TO RELATED APPLICATIONS

This is a National Phase application of International Application No. PCT/EP2020/051456, filed Jan. 22, 2020, which claims the benefit of and priority to EP application Ser. No. 19/000,057.0, filed on Jan. 30, 2019, which are herein incorporated by reference for all purposes.

FIELD OF THE INVENTION

The present application relates generally to a method and system for three-dimensional (3D) imaging and, more particularly, to a method and system for dynamically providing real-time feedback about a quality of data being collected during intraoral scanning, said real-time feedback being provided at the intraoral scan site.

BACKGROUND OF THE INVENTION

Various options exist available for treating dental defects such as by designing restorations or orthodontic aligners. During such treatments, a clinician may scan a patient's intraoral cavity to create a three-dimensional model of the patient's intraoral cavity. The collection of quality 3D data may be critical when reconstructing three-dimensional images of an object. During intraoral scanning the clinician may regularly change his/her view between the patients intraoral cavity and a display by orienting the camera in the mouth of the patient for 3D data acquisition as well as controlling the scan process from the display in order to, for example (i) ensure that the data acquisition is ongoing and is not interrupted, (ii) check if a registration of a scan body or buccal cavity is successful, (iii) check which regions of the intraoral cavity have already been scanned and which regions have not been scanned yet and/or (iv) ensure that acquired 3D data is sufficient for clinical purposes and/or enough individual optical 3D measurements have been acquired for accurate reconstruction of virtual teeth.

A main drawback of this manual process may be that it is tedious, time consuming and the user may lose orientation when looking back and forth between the patient's mouth and the screen. Moreover current systems may not indicate if acquired data is sufficient or if some intra-oral sites should be scanned again. Further, by simply looking at a display, a clinician may miss reconstruction inaccuracies that may not be detected by the untrained eye.

U.S. Pat. No. 9,838,670B2 discloses for "point and click" camera whether a current position of the camera is adequate for capturing a second image based on a first position of a first image. It provides a method for three-dimensional imaging including storing a first two-dimensional image of field of view of a scanning device at a first position where a first three-dimensional view of the object is captured with the scanning device, estimating location metric of a second two-dimensional image of field of view of the scanning device at a second position relative to the first image while the scanning device is being moved from the first position to the second position, and generating instructions on providing feedback to the user based on the location metric, wherein said feedback is provided to indicate if said second position is adequate for capturing a second three-dimensional view.

U.S. Pat. No. 7,940,260B2 discloses a scanning system that may acquire three-dimensional images as an incremental series of fitted three-dimensional data sets by testing for successful incremental fits in real time and providing a variety of visual user cues and process modifications depending upon the relationship of newly acquired data to previously acquired data.

U.S. Pat. No. 4,837,732A discloses a method of facilitating acquisition of data defining the three-dimensional shape of prepared teeth and their immediate vicinity including displaying on a video display a live image from a scan head, manually orienting the scan head relative to the prepared teeth while observing the image of the teeth on said video display, thereafter generating from data produced by said scan head in a selected orientation corresponding depth and contrast images, and thereafter processing said depth image based on said contrast image.

SUMMARY OF THE INVENTION

Existing limitations associated with the foregoing, as well as other limitations, can be overcome by the method according to claim 1 and the system according to claim 11 for dynamically providing visual feedback about a quality of data collected during intra-oral scanning. Images or light patterns may be projected onto an object such teeth for 3D measurement and for relaying feedback about a quality of the 3D measurement to the user. Herein unsuccessful registrations and holes/gaps (i.e. surface regions that were not scanned) may be corrected by informing the user to repeat scans at corresponding locations in the intra-oral cavity.

In an aspect herein, the present invention provides a method for dynamically providing visual feedback about a quality and/or other predetermined property of scan data collected during intra-oral scanning, said visual feedback provided at or near an intra-oral scanning site, the method comprising the steps of: providing a plurality of individual optical 3D measurements of the surface of an intra-oral cavity; determining if each of the plurality of individual optical 3D measurement as well as the accumulated plurality of 3D measurements meet a predetermined recording criteria; and projecting said visual feedback including a successful registration feedback and/or a non-successful registration feedback onto surfaces of the intraoral cavity corresponding to the individual optical 3D measurements based on the determining step.

According to another aspect of the present invention a method is provided including one or more combinations of the following: (i) wherein said successful registration feedback and/or non-successful registration feedback are projected as part of a projection image which includes a first region corresponding to projection rays for 3D measurement and a second region corresponding to the successful registration feedback and/or the non-successful registration feedback, (ii) further comprising providing said visual feedback in real-time, (iii) further comprising extracting 3D coordinates of each of the plurality of individual optical 3D measurements to determine if the optical 3D measurement has been previously scanned, (iv) wherein each of the plurality of individual optical 3D measurements overlaps with another individual optical 3D measurement to form an overlapping area, (v) wherein the predetermined recording criteria is selected from the group consisting of (a) an adequate size of the overlapping area, (b) an adequate waviness of an object surface in the overlapping area, (c) an adequate roughness of the object surface in the overlapping area, (d) an adequate number of characteristic geometries in the overlapping area, (e) an adequate image quality/resolution in the overlapping area and/or (f) regions of the intra-oral cavity not contained in an accumulated data set.

In another aspect of the present invention, a system for dynamically providing visual feedback about a quality of data collected during intra-oral scanning, said visual feedback provided at or near an intra-oral scanning site is provided, the system comprising at least one processor configured to: provide a plurality of individual optical 3D measurements of a plurality of measurement surfaces of an intra-oral cavity; determine if each of the plurality of individual optical 3D measurements meets a predetermined recording criteria; and project said visual feedback including a successful registration feedback and/or a non-successful registration feedback onto surfaces of the intraoral cavity corresponding to the individual optical 3D measurements based on the determining step.

According to another aspect of the present invention the system is provided including one or more combinations of the following: (i) wherein the processor is further configured to project said successful registration feedback and/or non-successful registration feedback as part of a projection image which includes a first region corresponding to projection rays for 3D measurement and a second region corresponding to the successful registration feedback and/or the non-successful registration feedback, (ii) wherein the processor is further configured to provide said visual feedback in real-time, (iii) wherein the processor is further configured to extract 3D coordinates of each of the plurality of individual optical 3D measurements to determine if the optical 3D measurement has been previously scanned, (iv) further comprising at least one projector and at least one image sensor in communication with the processor, (v) wherein the projector is housed inside an intra-oral camera, (vi) wherein the projector is separate from an intra-oral camera, (vii) wherein the projector is selected from the group consisting of a Digital Light Processing projector, a Light Emitting Diode projector, a Laser projector, a Liquid Crystal on Silicon projector and an Liquid Crystal Display projector.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein.

DETAILED DESCRIPTION OF THE INVENTION

In accordance with example aspects described herein, a method and system for dynamically providing feedback about a quality of data being collected during intraoral scanning, as well as feedback about which areas of an intraoral cavity are already acquired, said feedback being provided at/or near the intraoral scan site. However, it may be appreciated that the inventive concepts disclosed herein may not limited to such applications, and may be usefully employed in a variety of imaging applications. For example, the system and method described herein may be usefully employed in non-intraoral applications, non-dental applications or other applications where the imaging could be enhanced by a real-time feedback or where the generation of an object surface in three dimensions may be based on stitching of several 3D views captured at arbitrary orientation relative to the object with a scanning device under free control of a user. All such variations and alternative embodiments as would be apparent to one of ordinary skill in the art are intended to fall within the scope of the invention.

The present invention may provide a method and system for providing feedback during intraoral scanning by images or light patterns projected onto an object such teeth. The invention may therefore enable intraoral scanning in which a display/monitoring screen may not be needed and wherein unsuccessful registrations gaps/holes may be corrected by informing a user to repeat scans at corresponding locations in the intra-oral cavity.

System for Modeling and Visualizing a Dental Solution

Figure 1:
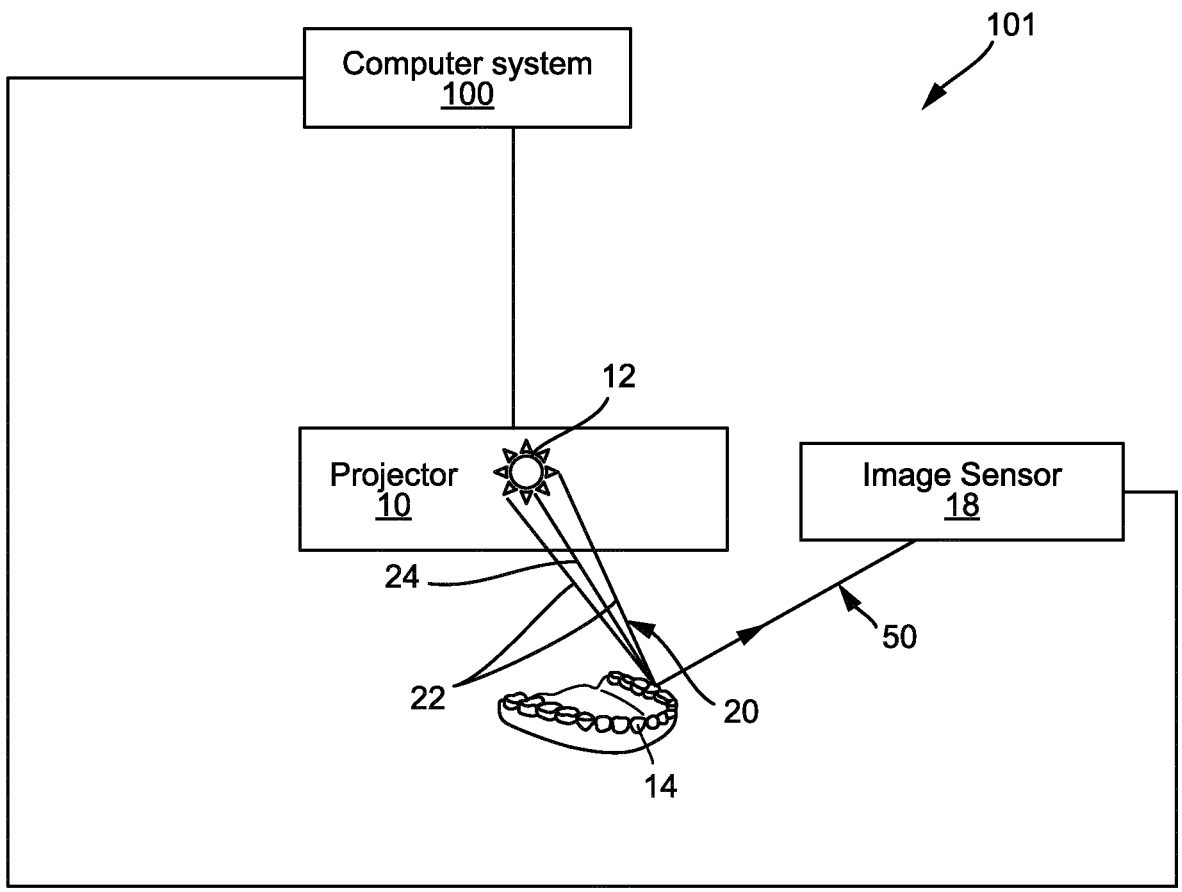
FIG. 1 is a block diagram illustrating a system according to an embodiment of the present invention.
Figure 7:
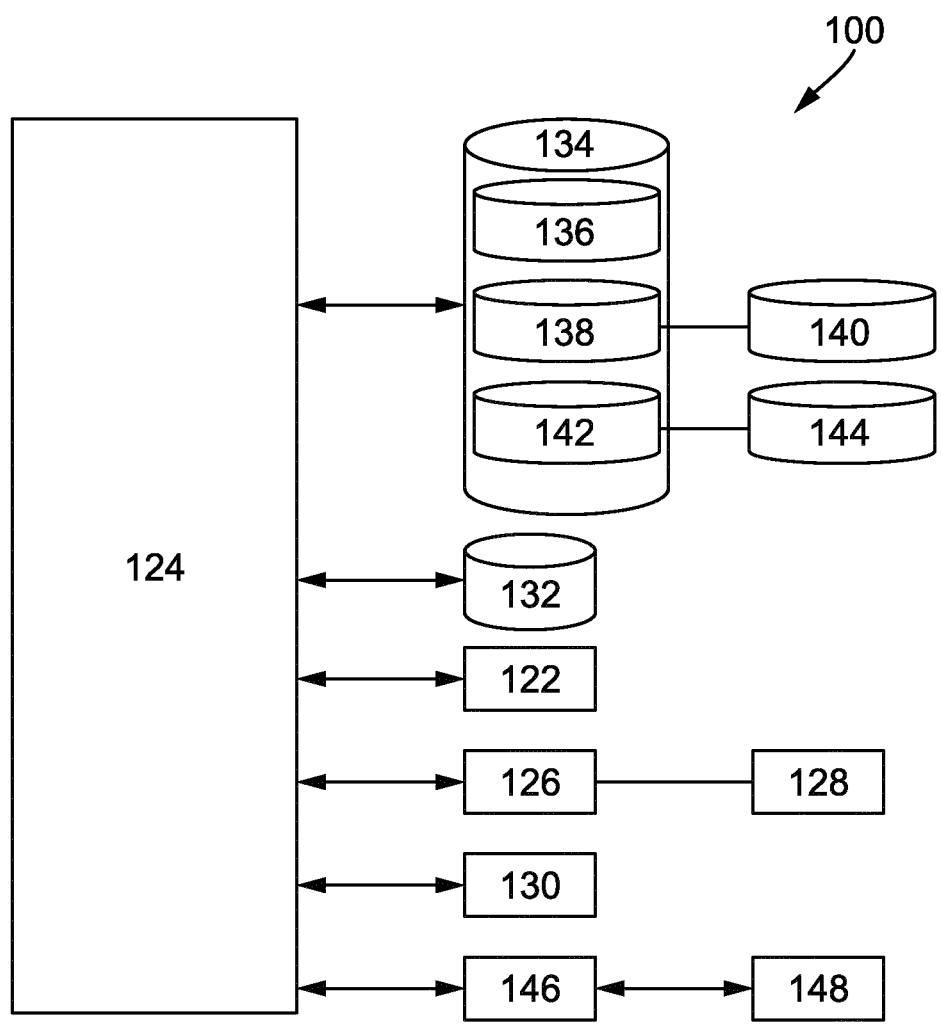
FIG. 7 is a block diagram showing a computer system according to an exemplary embodiment of the present invention.

FIG. 1 illustrates a block diagram of a light guidance system 101 comprising at least one projector 10 having a light source 12, at least one image sensor 18 (e.g. a 3D image sensor) and a computer system 100 with at least one computer processor 122 (FIG. 7). The projector 10 and image sensor 18 may be in communication with the computer system 100. The projector 10 may be a projector housed within a camera such as an intraoral camera 32. Alternatively, the projector 10 may be a separate projector such as a digital light projector outside the intra-oral camera 32. Projectors 10 may work on a principle of filtering a light source 12 based on an image to be displayed. A lens (not shown) may then be used to transfer the image to a surface on which the image may be displayed. Different kinds of projectors may be used, including Digital Light Processing (DLP) projectors which may be based on Digital Micromirror Device (DMD) technology wherein an array of microscopic mirrors may be configured to tilt either toward the light source 12 in the projector 10 or away from it in order to create a light or dark pixel on a projection surface. Other kinds of projectors may include Light Emitting Diode (LED) projectors, Laser projectors, Liquid Crystal on Silicon (LCoS) projectors and Liquid Crystal Display (LCD) projectors. One or more projectors 10 may be used for projecting one or more projection images 48 (FIG. 5) on a surface such as a tooth surface 28 (FIG. 4) and may be constructed and operated in accordance with at least one exemplary embodiment herein. The projector may illuminate a 3D measuring field as well as surfaces outside the measuring field. Herein, information about already acquired/scanned surfaces, surfaces not yet acquired as well as other 3D measurement information (such as scan-body registration)

may be visually superimposed by using a projected pattern or color onto surfaces outside the measuring field. In this way the user can control the scan process while looking into the mouth of the patient. Said projection may be dynamic, wherein an illumination beam 20 from the projector 10 may be controlled to produce said one or more projection images 48 at preferably predetermined time intervals and wherein at least a part of the illumination beam 20 may be reflected into a monitoring beam 50 for 3D measurement.

Figure 2:
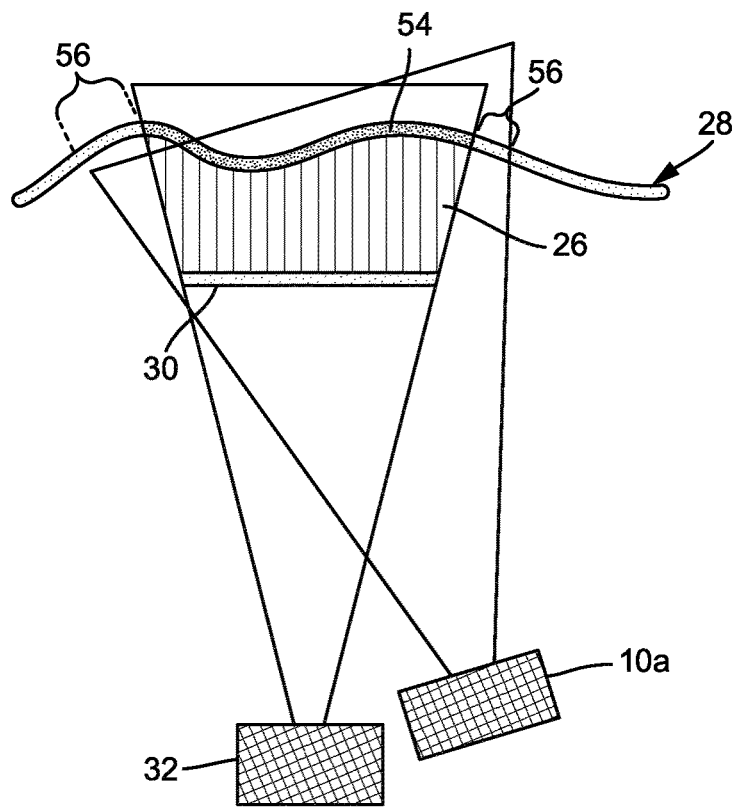
FIG. 2 is a diagram illustrating inner and outer rays according to an exemplary embodiment of the present invention.
Figure 4:
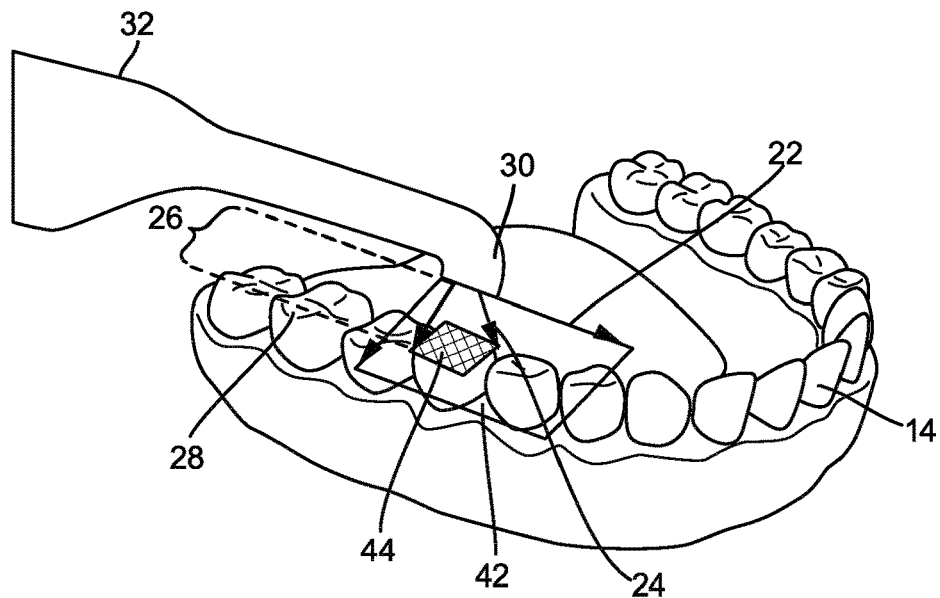
FIG. 4 is a perspective view showing a projection with a camera according to an exemplary embodiment of the present invention.
Figure 5:
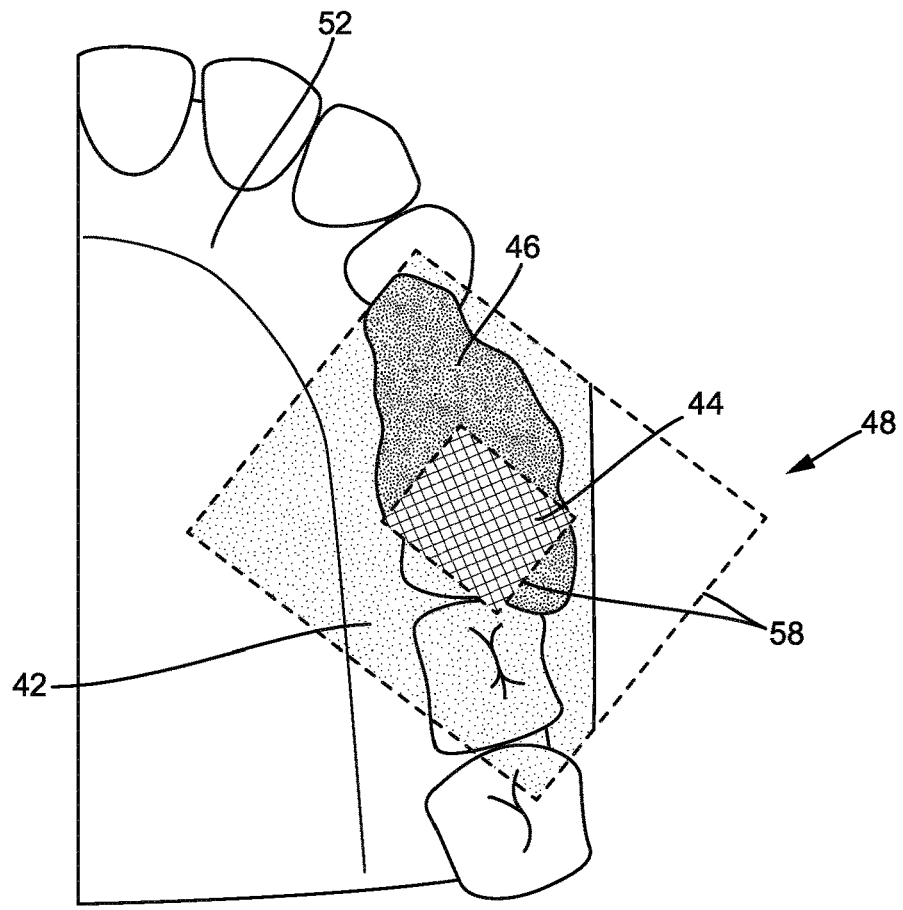
FIG. 5 is a top view illustrating a projection image according to an exemplary embodiment of the present invention.

As shown in FIG. 4, each projection image 48 may include a first/inner region 44 corresponding to projection rays for 3D measurement and/or a second/outer region 42 corresponding to projection rays for providing a user with visual feedback and vice versa. A shape of the inner region 44 and/or outer region 42 may be pre-determined, for example, square, rectangle, circle etc. In an exemplary embodiment of the present invention as shown in FIG. 2, an intraoral camera 32 may be electrically paired with a separate projector 10a with the projector 10a projecting at least a portion of projection image 48 on a tooth surface 28 for user feedback. The intra-oral camera 32 itself may also have a projector 10 for projecting at least another portion of the projection image 48 for 3D measurement. Said pairing may be achieved by using a common controller such as a computer processor 122 to simultaneously control illumination of the tooth surface 28 by the illumination beam 20 from the projector 10a and intra-oral camera 32 and recording of the reflected monitoring beam 50.

Figure 3:
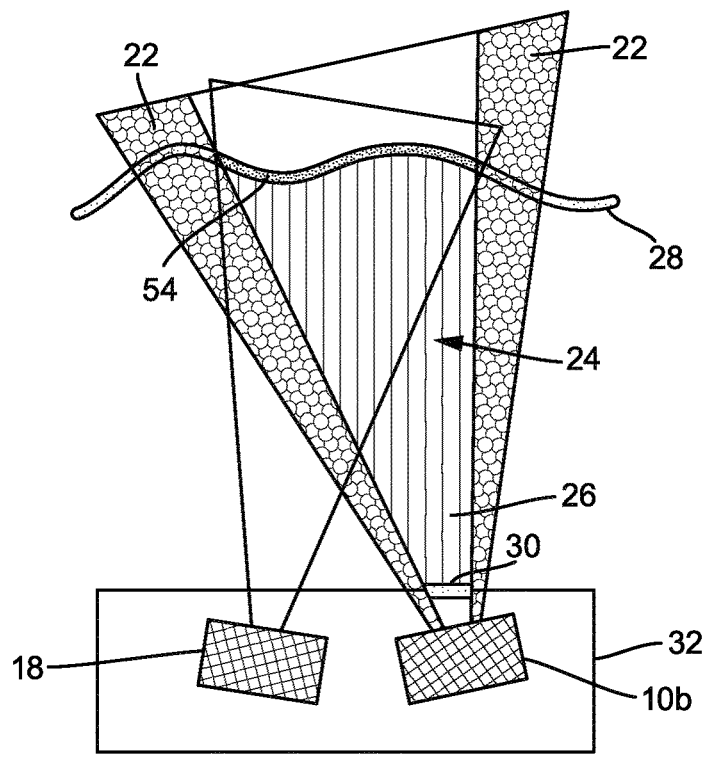
FIG. 3 is a diagram illustrating a measurement volume according to an exemplary embodiment of the present invention.

In another exemplary embodiment of the present invention as shown in FIG. 3, a projector 10b of the intra-oral camera 32 may be configured to project the projection image 48 on the tooth surface 28 for both 3D measurement and user feedback. Herein, inner rays 24 of the illumination beam 20 may be configured to produce the inner region 44 of the projection image 48 for 3D measurement and/or outer rays 22 of the illumination beam 20 may be configured to produce the outer region 42 of the projection image 48 for user feedback and vice versa.

Therefore, the projector 10b of the intra-oral camera 32 may be configured to project the illumination beam 20 comprising both 3D measurement rays and user feedback rays.

In a further embodiment, the projector 10 may be configured to alternate between projecting the 3D measurement rays and projecting the user feedback rays.

In a further embodiment, the intra-oral camera 32 may be configured so that the reflected monitoring beam 50 for 3D measurement includes all or substantially all portions of the illumination beam 20 that are configured for 3D measurement. Further portions of the illumination beam 20 configured for 3D measurement (inner rays of the illumination beam 24) may be configured to be structured illumination patterns and/or may be modulated before illumination. By using various structured illumination patterns, 3D surface profiles of tooth surfaces 28 may be measured. Moreover, by modulating with a predetermined frequency, only signals corresponding to that frequency may be detected by the image sensor 18 for further processing.

Method for Modeling and Visualizing a Dental Solution.

Figure 6:
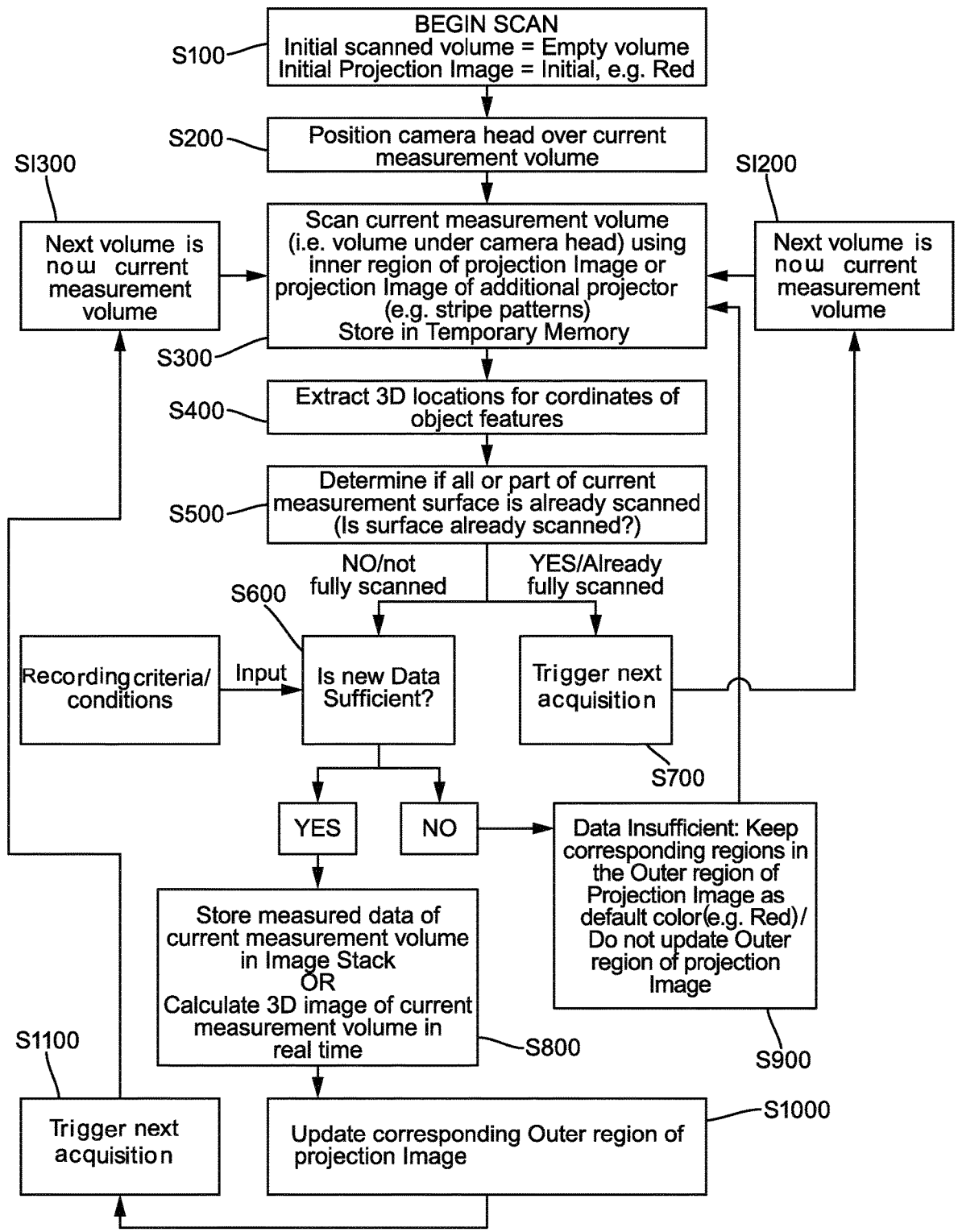
FIG. 6 is a flow chart showing a method according to an exemplary embodiment of the present invention.

Having described the light guidance system 101 of FIG. 1, a method for dynamically providing feedback about a quality of data being collected during intraoral scanning will now be further described in conjunction with FIG. 6.

The invention may include producing and updating a 3D model through a scanning process by a user moving an intraoral camera head 30 over a location (e.g. a tooth surface 28). The scan may begin as shown in Step S100 wherein a memory of a computer system 100 may store a volume of the intra-oral cavity 52 as an empty volume which may be subsequently updated as scanning progresses. After placing the intra-oral camera head 30 over the tooth surface in Step S200, a projector 10 of the intra-oral camera 32 may project an initial default projection image over a region of the intra-oral cavity 52, to show that image data have not been acquired yet for processing.

In an example embodiment herein, the projector 10 may be configured to provide a successful registration feedback signifying a successful registration of the current measurement surface 54 and a non-successful registration feedback signifying a non-successful registration of the current measurement surface 54 e.g. a blue colored rectangle or striped pattern for 3D measurement (the inner region 44 of the projection image 48, FIG. 5, which also corresponds to a current measurement surface 54) may be inside a larger red colored rectangle (outer region 42 of the projection image 48 corresponding to other surfaces 56 of the cavity), the red colored rectangle signifying a non-successful registration of intra-oral surfaces on which said feedback is projected. Upon any successful registration, corresponding surfaces 46 of the successful registration in the outer region 42 may receive a successful registration feedback, e.g. green light, signifying that said corresponding surfaces of the successful registration 46 have been successfully registered. In an embodiment herein, the outer region 42 may receive an initial non-successful registration feedback signifying that scanning has not begun. Of course other implementations of the shapes and/or colors of the different components of the projection image 48 may be realized without departing from the scope of the invention.

Preferably, inner rays 24 of the illumination beam 20 as shown in FIG. 3, which may be configured to form the inner region 44 of the projection image 48 (or rays from the intra-oral camera 32 in a light guidance system 101 having a separate projector 10a for user feedback as shown in FIG. 2), may pass through a current measurement volume 26 (i.e. volume under the intra-oral camera head 30) onto at least a portion of a tooth surface 28 to be measured, said portion of the tooth surface 28 being the current measurement surface 54 (Step S300). The outer rays 22 of the illumination beam 20 may coincide on other surfaces 56 of the cavity within a predefined boundary 58 within which feedback about whether or not corresponding points on said other surfaces 56 have been previously scanned may be visually relayed to the user. At the beginning of the scan, a default feedback may be relayed to the user to show that said other surfaces 56 have not been previously scanned.

As shown in Step 300, the inner rays 24 of the illumination beam may be substantially reflected off the current measurement surface 54 towards an image sensor 18 of the intra-oral camera 32 for further processing. Herein, 3D coordinates of the current measurement surface 54 may be extracted in Step S400 to determine if all or part of the current measurement surface 54 has been previously registered (Step S500). If the current measurement surface 54 or any portion of the current measurement surface has not been previously acquired, the corresponding new 3D data (e.g. xyz coordinates) of unregistered portions may be stored by determining if the new 3D data and/or accumulated 3D data are sufficient according to one or more predetermined recording criteria/conditions (Step S600) said predetermined recording criteria including for example, whether or not the new 3D data and/or accumulated 3D data have a desired predetermined resolution, predetermined noise level, predetermined 3D point density, and/or inconsistencies between individual optical 3D measurements. If the predetermined recording criteria is satisfied, the new 3D data may be stored in an image stack for post processing or the 3D data may be used to create a real-time 3D reconstruction of the intraoral cavity as shown in Step S800. The outer region 42 of the projection image 48 corresponding to the new 3D data may then be updated in Step S1000 to relay to the user when the intra-oral camera 32 camera position changes to a new measurement surface that the previous measurement surface has been sufficiently recorded according to predetermined recording criteria. Herein, a need to constantly look at a monitor to track the progress of an ongoing intra-oral scan and make necessary adjustments may be eliminated or substantially eliminated as a visual feedback for the user may be shown in the vicinity of the intra-oral surfaces being scanned.

Alternatively, if the current measurement surface 54 has been previously scanned, the next acquisition may be triggered (Steps S700, S1200) to continue recording other surfaces.

Moreover, if the new data obtained in Step S600 is insufficient according to the predetermined recording criteria, the default feedback for the user signifying that the current measurement surface 54 has not been scanned/registered may remain unchanged or may be changed in a predetermined way to signify that the current measurement surface 54 has not been scanned.

In an exemplary embodiment of the present invention, determining if the new data is sufficient, as shown in Step S600 may be achieved as follows. A plurality of three-dimensional optical measurements may be received by the processor 122, said plurality of three-dimensional optical measurements respectively corresponding to a plurality of current measurement surfaces 54, of one or more dental objects generated by the intra-oral camera 32 according to one or more recording sequences. Each optical measurement/image may overlap with another optical measurement to form a plurality of overlapping areas (not shown), and each overlapping area may include a later optical image and an earlier optical image, the later optical image being generated at a later imaging position in the recording sequence than the earlier optical image. Herein, for each overlapping area, it may be determined whether the overlapping area fulfills one or more predetermined recording criteria. The predetermined recording criteria may include, for example, (i) an adequate size of the overlapping area, (ii) an adequate waviness of an object surface in the overlapping area, (iii) an adequate roughness of the object surface in the overlapping area, (iv) an adequate number of characteristic geometries in the overlapping area, (v) an adequate image quality/resolution in the overlapping area and/or (vi) regions of the intra-oral cavity not contained in an accumulated data set.

If the predetermined recording criteria is/are satisfied, the later optical 3D measurement may be added/registered to an image sequence that includes the earlier optical 3D measurement, and/or a corresponding global 3D image of the sequence may be reconstructed in real time or at a later time (Step 800). It will be appreciated by a person of ordinary skill in the art that other registration step may be employed herein without departing from essential attributes of the invention.

Based on a relative position of the camera head 30 from the surfaces being measured, the "x,y,z" coordinates of images in the sequence and/or the reconstructed global 3D image, the projector 10 may be configured to project a feedback to the user (Step S1000) signifying which corresponding portions of the intraoral cavity have been sufficiently recorded and which regions have not been sufficiently recorded, e.g. green light may be projected to portions of the intraoral cavity that have been sufficiently recorded and red light may be projected to portions of the intraoral cavity that have not been recorded or have not been sufficiently recorded yet. This may be repeated in real-time for all other surface and recording sequences as shown in Steps S1100, S1300. Therefore the user may not need to constantly look at a monitor to examine the progress of the scanning procedure since the quality of registration during the scan may be provided to the user in an ongoing and as such unsuccessful registrations may be corrected by repeating scans at corresponding locations in the intra-oral cavity.

In another workflow, the current measurement surface 54 may be scanned and a corresponding optical image acquired. The corresponding optical image may contain a 3D point cloud, information about a position of the intra-oral camera 32 relative to the 3D point cloud. The corresponding optical image may be registered to an accumulated 3D data set from previous measurements and added to the accumulated data set if there is an overlap (if it fits, according to, for example, the Iterative Closest Point (ICP) algorithm). Positional information about the intra-oral camera 32 relative to the accumulated data set may be known. If there is no overlap (if it does not fit), the intra-oral camera 32 may lose track of its position and the user may move the intra-oral camera 32 to a position where the new measurement may be registered and added to the 3D data set. The accumulated data set may then be analyzed for holes/gaps in the data, low point density and/or inconsistencies. Further, the analysis may include or be a determination of if the temperature of the intra-oral camera 32 exceeds a predetermined value. Based on the result of the analysis and the position of the intra-oral camera 32 relative to the accumulated data set a projection image 48 for the projector 10 may be generated such that: (i) regions under the camera that are not represented accumulated data set may be indicated by a first color in the projection image 48 (for example red), (ii) regions like holes/gaps, low density regions and inconsistencies may be indicated in the projection image 48 by a second color (for example blue) and/or (iii) regions containing valid data (regions that are represented the accumulated data set) are indicated by a third color (for example green). Herein the intra-oral camera 32 may be moving and directly triggering the next acquisition, once the current acquisition is processed. In an embodiment herein, the intra-oral camera 32 may determine the direction of projection of rays from a relative transformation of a prior 3D measurement to the accumulated data set, Herein, the intra-oral camera 32 may have information about its position relative to the accumulated 3D data set. Based on this information the intra-oral camera 32 may determine the position (relative to the camera window) of regions that were not sufficiently recorded (red regions in the feedback projection) and project corresponding rays to said regions. Moreover, in an exemplary embodiment, information about a scan workflow may be projected based on the determined position information. For example, the visual feedback may include information about a next region of the intra-oral cavity 52 for acquisition, fogging on windows of the intra-oral camera based on determined temperature of the intra-oral camera 32, an indication to remove the camera from the intra-oral cavity 52 based on said fogging, etc. The temperature indication may be followed by a warning such as one showing that the intra-oral camera 32 may shut down soon. Further an indication of fogging may be followed by an instruction such as an instruction to heat or blow off the camera.

Further, by using an illumination that may alternate between projection rays for providing feedback and projection rays for 3D measurement, interference the projection rays for providing feedback and projection rays for 3D measurement may be reduced or eliminated.

Of course another method similar to methods described herein for modeling and visualizing a dental solution may be realized in light of descriptions provided.

In view of the foregoing description, it may be appreciated that the example embodiments described herein provide a method for dynamically providing feedback about a quality of data being collected during intraoral scanning.

Computer System for Modeling and Visualizing a Dental Solution

Having described the light guidance system 101 and method, reference will now be made to FIG. 7, which shows a block diagram of a computer system 100 that may be employed in accordance with at least some of the example embodiments described herein. Although various embodiments may be described herein in terms of this exemplary computer system 100, after reading this description, it may become apparent to a person skilled in the relevant art(s) how to implement the disclosure using other computer systems and/or architectures.

In an embodiment herein the computer system 100 may form a part of the light guidance system 101. In another embodiment herein, the computer system may be separate from the light guidance system 101. Although various embodiments may be described herein in terms of this exemplary computer system 100, after reading this description, it may become apparent to a person skilled in the relevant art(s) how to implement the disclosure using other computer systems and/or architectures.

The computer system 100 may include at least one computer processor 122. The computer processor 122 may include, for example, a central processing unit, a multiple processing unit, an application-specific integrated circuit ("ASIC"), a field programmable gate array ("FPGA"), or the like. The processor 122 may be connected to a communication infrastructure 124 (e.g., a communications bus, or a network). In an embodiment herein, the processor 122 includes a CPU that obtains an image stack or sequence of images from a signal preprocessing unit of the intra-oral camera 32. The stack may be temporarily stored in memory and then analyzed to determine is the images meet a predetermined recording criteria as described in the methods discussed herein. The processor 122 may then operate the projector 10 and/or light source 12 to control the illumination beam 20.

The computer system 100 may optionally include a display interface (or other output interface) 126 which may forward video graphics, text, and other data from the communication infrastructure 124 (or from a frame buffer (not shown)) for display on a display unit 128 (which, in one example embodiment, may form or be included in the display unit 128 of FIG. 1), though the display interface 126 and/or display unit 128 may not be needed.

The computer system 100 may also include an input unit 130 that may be used by a user of the computer system 100 to send information to the computer processor 122. The input unit 130 may include a trackball or other input device such as a keyboard and/or touchscreen monitor.

In one example, the display unit 128, the input unit 130, and the computer processor 122 may collectively form a user interface.

One or more steps of generating the controlling the system 101 to generate 3D images and feedback for the user may be stored on a non-transitory storage device in the form of computer-readable program instructions. To execute a procedure, the processor 122 loads the appropriate instructions, as stored on storage device, into memory and then executes the loaded instructions.

The computer system 100 of FIG. 6 may comprise a main memory 132, which may be a random access memory ("RAM"), and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 may read from and/or write to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 may carry signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs may include computer-executable instructions which, when executed by the computer processor 122, cause the computer system 100 to perform the methods described. Accordingly, the computer programs may control the computer system 100 and other components of the light guidance system 101.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, may cause the computer system 100, and more generally the light guidance system 101 in some embodiments, to perform all or some of the methods described herein.

Lastly, in another example embodiment hardware components such as ASICs, FPGAs, and the like, may be used to carry out the functionality described herein. Implementation of such a hardware arrangement so as to perform the functions described herein will be apparent to persons skilled in the relevant art(s) in view of this description.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

The invention claimed is:

1. A method of controlling a system for dynamically providing visual feedback about scan data collected during intra-oral scanning, said visual feedback provided at or near an intra-oral scanning site, the system comprising: at least one processor; at least one projector and at least one image sensor in communication with the processor, the method comprising:
    providing a plurality of individual optical 3D measurements of a plurality of measurement surfaces of an intra-oral cavity;
    determining if at least one of the plurality of individual optical 3D measurements and/or an accumulated plurality of optical 3D measurements meet predetermined recording criteria; and
    projecting said visual feedback onto surfaces of the intraoral cavity corresponding to the individual optical 3D measurements based on the determining
    wherein the predetermined recording criteria is selected from the group consisting of (i) an adequate size of the overlapping area, (ii) an adequate waviness of an object surface in the overlapping area, (iii) an adequate roughness of the object surface in the overlapping area, (iv) an adequate number of characteristic geometries in the overlapping area, and (v) an adequate 3D point density in the overlapping area and/or regions of the intra-oral cavity not contained in an accumulated data set.

2. The method according to claim 1, wherein said visual feedback is projected as part of a projection image which includes a first region corresponding to projection rays for 3D measurement and a second region corresponding to the visual feedback.

3. The method according to claim 2, wherein the first region corresponding to projection rays for 3D measurement and the second region corresponding to the visual feedback overlap at least partially.

4. The method according to claim 2, wherein said visual feedback is projected using an illumination beam which produces the first region as an inner region of the projection image from inner rays of the illumination beam and which produces the second region as an outer region of the projection image using outer rays of the illumination beam and vice versa.

5. The method according to claim 4, further comprising alternating the illumination beam between the inner rays and the outer rays.

6. The method according to claim 1, further comprising providing said visual feedback in real-time.

7. The method according to claim 1, further comprising extracting 3D coordinates of each of the plurality of individual optical 3D measurements to determine if corresponding regions of the intra-oral cavity have been previously scanned.

8. The method according to claim 1, wherein each of the plurality of individual optical 3D measurements overlaps with another individual optical 3D measurement to form an overlapping area.

9. The method according to claim 1, wherein the visual feedback includes feedback about a successful registration, feedback about a non-successful registration, a feedback about unscanned areas of the intra-oral cavity, feedback about a user workflow, a feedback about a temperature of the intra-oral camera, or a feedback about a warning.

10. A system for dynamically providing visual feedback about scan data collected during intra-oral scanning, said visual feedback provided at or near an intra-oral scanning site, the system comprising:
    at least one processor configured to execute the method according to claim 1;
    at least one projector; and
    at least one image sensor in communication with the processor.

11. The system of claim 10, wherein the projector is housed inside an intra-oral camera.

12. The system according to claim 10, wherein the projector is separate from an intra-oral camera having the at least one image sensor.

13. The system according to claim 10, wherein the projector is selected from the group consisting of a Digital Light Processing projector, a Light Emitting Diode projector, a Laser projector, a Liquid Crystal on Silicon projector, and a Liquid Crystal Display projector.

* * * * *